(12) United States Patent
Duflot et al.

(10) Patent No.: US 8,007,850 B2
(45) Date of Patent: Aug. 30, 2011

(54) METHOD FOR MAKING A POWDER CONTAINING CRYSTALLINE PARTICLES OF GLUCOPYRANOSYL-ALDITOLS

(75) Inventors: Pierrick Duflot, La Couture (FR); Liuming Zhou, Macomb, IL (US)

(73) Assignee: Roquette Freres, Lestrem (FR)

( * ) Notice: Subject to any disclaimer, the term of this patent is extended or adjusted under 35 U.S.C. 154(b) by 1205 days.

(21) Appl. No.: 11/311,142

(22) Filed: Dec. 20, 2005

(65) Prior Publication Data
US 2006/0147597 A1    Jul. 6, 2006

(30) Foreign Application Priority Data

Dec. 21, 2004   (FR) ...................................... 04 13660

(51) Int. Cl.
*A23L 1/236* (2006.01)
(52) U.S. Cl. ........................... 426/548; 426/443; 127/34
(58) Field of Classification Search ................. 426/443, 426/471, 548; 127/29, 34
See application file for complete search history.

(56) References Cited

U.S. PATENT DOCUMENTS 6,755,914 B2 * 6/2004 Ueno et al. ...................... 127/29

2003/0101989 A1   6/2003 Ueno et al.

FOREIGN PATENT DOCUMENTS

| EP | 1 172 370 A1 | 1/2002 |
| EP | 1 284 102 A1 | 2/2003 |
| WO | WO 00/64916 | 11/2000 |

* cited by examiner

*Primary Examiner* — Leslie Wong
(74) *Attorney, Agent, or Firm* — Young & Thompson

(57) ABSTRACT

The invention relates to a method for making a powder containing crystalline particles of glucopyranosyl-alditols, including the continuous mixing of a glucopyranosyl-alditol syrup with a dry matter content of at least 80% by weight and a glucopyranosyl-alditol content of at least 95% by weight, preferably of at least 98% by weight based on dry matter, the mixing being carried out by simultaneously dispersing the glucopyranosyl-alditol syrup and germs containing glucopyranosyl-alditols in an open rotary container containing (glucopyranosyl-alditol)-based granules, whereby the glucopyranosyl-alditol syrup and the germs containing glucopyranosyl-alditols are mixed at the surface of the (glucopyranosyl-alditol)-based granules contained in the container, recovering the (glucopyranosyl-alditol)-based granules from the container and crystallizing the glucopyranosyl-alditols contained in the granules, the (glucopyranosyl-alditol)-based granules in the container being kept in motion by rotating the container.

19 Claims, No Drawings

METHOD FOR MAKING A POWDER CONTAINING CRYSTALLINE PARTICLES OF GLUCOPYRANOSYL-ALDITOLS

BACKGROUND OF THE INVENTION

Field of the Invention

The present invention relates to a method for the continuous making of a powder containing crystalline particles of glucopyranosyl-alditols.

DESCRIPTION OF THE RELATED ART

"Glucopyranosyl-alditols" within the meaning of the invention, means compounds selected from the group consisting of 1-O-α-D-glucopyranosyl-D-mannitol (1,1 GPM), 6-O-α-D-glucopyranosyl-D-sorbitol (1,6 GPS) and 1-O-α-D-glucopyranosyl-D-sorbitol (1,1 GPS).

These glucopyranosyl-alditols are the result of hydrogenation of isomaltulose and trehalulose, themselves produced by isomerisation of saccharose by isolated enzymatic activities of particular microorganisms.

The most known of these microorganisms belong to the genera *Protaminobacter* (such as *P. rubrum* CBS 547.77), *Erwinia* (such as *E. rhapontici* NCPPB 1578), *Serratia* (such as *S. marcescens* NCIB 8285 or *S. plymouthica* ATCC 15928), *Leuconostoc* (such as *L. mesenteroides* NRRL B-521f or ATCC 10830a), *Pseudomonas* (such as *P. mesoacidophila* MX-45), *Agrobacterium* (such as *A. radiobacter* MX-232), *Klebsiella* or *Enterobacter* sp.

Isomaltulose and trehalulose may be hydrogenated as a mixture or separately (the separation of isomaltulose from trehalulose being achieved in particular by crystallization or chromatographic techniques).

Although hydrogenation of isomaltulose alone should theoretically generate an equimolar mixture of 1,6 GPS and 1,1 GPM, it was shown that the proportion of each of both isomers is actually of between 43 and 57%.

These mixtures of 1,6 GPS and 1,1 GPM are generally marketed in their crystallized form, under the brand names ISOMALT® or PALATNIT®.

In the same way, hydrogenation of trehalulose alone leads to obtaining a mixture of 1,1 GPM and 1,1 GPS.

Glucopyranosyl-alditols, either alone or as a mixture, or even in variable relative proportions, are generally used as low calorie sweeteners. For example ISOMALT® is used in confectionery, in bakery products, in desserts, in jams, chocolate, chewing gum and in many dietary articles.

Conventional methods for crystallizing mixtures of the three glucopyranosyl-alditols generally require specific equipment combining evaporation in vacuo, actual crystallization and drying (*Carbohydrates in Industrial Synthesis*, edited by M. A. CLARKE, Verlag Dr Albert Bartens KG, Berlin, 1992, page 48).

However, these methods have the drawbacks that it is difficult to make the apparatus simple to use and that it is also difficult to operate continuously because of the long duration required for obtaining mixtures of crystals.

Indeed, these crystallization methods do not allow the totality of glucopyranosyl-alditols of the mother liquor to be purified in a single step. In order to optimize the crystallization yield, it is therefore necessary to proceed with two or three successive crystallization steps.

Now, it is known that it is difficult to crystallize 1,1 GPS per se, and that 1,1 GPS also perturbs crystallization of 1,6 GPS and 1,1 GPM. The enrichment of mother liquids in 1,1 GPS during successive crystallization steps thus makes the method complicated for crystallizing both isomers and reduces the efficiency thereof.

In order to find a remedy to this drawback, EP Patent 1 173 453 describes a method for crystallizing glucopyranosyl-alditols consisting of contacting a liquid, containing one or more dissolved glucopyranosyl-alditols, with fine solid particles containing one or more of said glucopyranosyl-alditols in suspension in a gas.

However, this method makes additional steps mandatory for substantial elimination of the solvent component of the mixture thereby obtained by introducing air heated to a temperature which may reach 250° C., and for treating the resulting glucopyranosyl-alditol material in sedimentation so as to recover a essentially solid material composition comprising a multitude of crystals from said glucopyranosyl-alditol(s).

It is still necessary to proceed with additional drying of said composition of glucopyranosyl-alditol crystals, and then with milling and sieving in order to finally obtain a product having glucopyranosyl-alditol particles containing a multitude of microcrystals randomly agglomerated with each other.

Another solution for obtaining the crystalline solid mixture of glucopyranosyl-alditols is described in EP Patent 1 172 370.

The method described in this patent, according to which one may obtain a solid crystalline mixture, comprising 20 to 70% of 1,1 GPM, 23 to 70% of 1,6 GPS and 2 to 25% of 1,1 GPS, consists in continuously introducing a hydrogenated mixture of isomaltulose and trehalulose (prepared from cane sugar) with crystalline germs of glucopyranosyl-alditols in an extruder provided with a thin and long cooling area.

More specifically, the method comprises:
- adding crystalline germs of glucopyranosyl-alditols at a temperature below the melting point of said crystalline germs of glucopyranosyl-alditols in an aqueous solution of glucopyranosyl-alditols having 2 to 10% by weight of moisture, and
- cooling and kneading said aqueous solution of glucopyranosyl-alditols in the presence of crystalline germs, so as to produce a magma of glucopyranosyl-alditols which is continually extruded from a nozzle.

Subsequent steps of rough disintegration, maturation, drying, etc., are also mentioned within the scope of producing a final powder product.

However, in this method, cooling is used for performing crystallization by increasing the oversaturation level of the solution. It is therefore necessary to reduce viscosity by heating the solution having a high concentration of glucopyranosyl-alditols at a high temperature so that the crystalline seeds are homogeneously dispersed within a short time.

This method has the drawback of absorbing an enormous amount of energy as it requires the forming of a massecuite, i.e., an oversaturated substance containing crystalline germs and having a viscosity which is lowered by heating at a high temperature (up to 140° C.) and a high pressure.

This particular heating apparatus also needs to be used in order to prevent deterioration of mixability and dispersibility resulting from an increase in viscosity due to lowering of temperature and it is critical to retain a low viscosity in order to disperse and mix the crystalline germs within a limited time.

On the other hand, the method also requires that the ratio 1,1 GPM/1,6 GPS/1,1 GPS of the seeds be also finely monitored so that it is identical with that of the solution of glucopyranosyl-alditols introduced into the extruder.

As a result for the forgoing, the crystallization methods of the prior art have the drawback of being expensive, complex and time-consuming.

SUMMARY OF THE INVENTION

The main object of the invention is to provide a method for making a powder containing crystalline particles of glucopyranosyl-alditols which is less sensitive to the aforementioned drawbacks and according to which a powder containing crystalline particles of glucopyranosyl-alditols may be efficiently obtained, with the desired properties.

The method for making crystalline particles of glucopyranosyl-alditols according to the invention does not require a very high concentration of glucopyranosyl-alditols, and neither requires any particular effort for monitoring or accurately measuring the temperature during the granulation/crystallization step.

Moreover, the method of the invention does not involve any formation of massecuite, nor the application of a shearing or kneading force, but is indeed simply based on concurrent coating, agglomeration and induction of crystallization by allowing the agglomerated mixture to mature at a temperature below the melting point of glucopyranosyl-alditols, in order to form solid granules.

DETAILED DESCRIPTION

According to the present invention, a method for making a powder containing crystalline particles of glucopyranosyl-alditol is provided, comprising continuous mixing of a glucopyranosyl-alditol syrup having a dry matter content of at least 80% by weight and a glucopyranosyl-alditol content of at least 95% by weight, preferably of at least 98% by weight, based on the dry matter, the mixing being carried out by simultaneously dispersing the glucopyranosyl-alditol syrup and germs containing glucopyranosyl-alditols in an open rotary container containing (glucopyranosyl-alditol)-based granules, whereby the glucopyranosyl-alditol syrup and the germs containing glucopyranosyl-alditols are mixed at the surface of the (glucopyranosyl-alditol)-based granules contained in the container, recovering the (glucopyranosyl-alditol)-based granules from the container and crystallizing the glucopyranosyl-alditols contained in said granules, the (glucopyranosyl-alditol)-based granules in the container being kept in motion by rotating the container.

When conducting the method of the invention, the glucopyranosyl-alditol syrup is preferably introduced into the container in a subdivided form, for example as drops or globules, jets or jet beams.

According to a preferred embodiment of the aforementioned method, a glucopyranosyl-alditol syrup, having a dry matter content of at least 80% by weight is brought to a temperature of at least 90° C. and is continuously mixed in a container with germs containing glucopyranosyl-alditols, wherein the germ/syrup ratio, the dimensions, the orientation of axis of rotation, and the rotational velocity of the container, are selected so that the recovered product from the container appears in the form of granules having an average diameter of about 100 to 50,000 μm.

The method of the invention may be conducted in an apparatus comprising:
- an open rotary container, with an axis of rotation which may be tilted horizontally,
- a means for bringing a portion of the glucopyranosyl-alditol syrup to an area located inside the container, above the mass which fills it partially, and dispersing it therein, preferably subdivided into the forms mentioned above and a few germs containing glucopyranosyl-alditols, and
- a means for achieving the mixture of the glucopyranosyl-alditol syrup and of germs containing glucopyranosyl-alditols at the surface of the moving mass partially filling the container.

The (glucopyranosyl-alditol)-based granules are preferably recovered by overflow at the outlet of the container and may be matured in order to increase their crystallinity by transferring the granules into a rotary cylinder with dimensional characteristics such that the residence time of the granules from the container is sufficient to provide crystallization of the glucopyranosyl-alditols.

The granules may then be transferred into a dryer in order to reduce residual moisture and then into a milling and sieving means.

Upon conducting the method according to the invention, a glucopyranosyl-alditol of syrup the type available commercially, and whose dry matter content is at least 70%, and having a glucopyranosyl-alditol content of at least 95% by weight, preferably of at least 98% by weight based on the dry matter, is dispersed at a temperature of about 80° C. inside an open rotary container as a tank or an open drum having an substantially flat bottom, the axis of rotation of which may be tilted on a horizontal plan by an angle of 25 to 45°.

An air spray nozzle was advantageously used for spraying the aqueous syrup on the rotary bed of germ material containing glucopyranosyl-alditols, in the pilot scale granulator.

As regards the transfer of germs containing glucopyranosyl-alditols in the aforementioned mixture and the constituent particles of which are used as germs containing crystallized glucopyranosyl-alditols, a particle size of about 100 μm is preferred.

The weight ratio in the mixture consisting of the germs containing glucopyranosyl-alditols and of the glucopyranosyl-alditol syrup is about 4/1, but may be reduced to 2/1, or even to 1/1, according to the desired performances.

The mixture is carried out at the surface of the moving mass partially filling the container. The relevant movement recalls a mass of pills inside a pill-making machine, and it was observed that granules are formed which are increasingly large, the largest granules tending to come to the surface of the moving mass.

The thereby obtained granules of glucopyranosyl-alditols are then matured in order to increase their crystallinity.

This maturation step may be performed by maintaining the moving granules at a temperature below the melting point of the granules, preferably at a temperature of 50 to 90° C., for 20 minutes to 2 hours in an air stream.

The granulated product is then dried in order to obtain residual moisture of between 2 and 10%.

The granules may then be milled up to the required particle size and then sorted by sieving; the particles removed by sieving may then be advantageously recycled to the aforementioned container in order to be used as germs containing glucopyranosyl-alditols.

The result powder containing crystalline particles of glucopyranosyl-alditols according to the invention is characterized by the fact that it has a compression value, according to test A, which is greater than 220 N, preferably between 250 and 400 N and still more preferentially between 280 and 350 N.

Compressibility of said powder containing crystalline particles of glucopyranosyl-alditols is determined according to the following test A, described in EP Patent 220 103, owned by the Applicant company. This test A consists in measuring the force, expressed in Newtons, which is representative of the compressibility of a powder containing crystalline particles of glucopyranosyl-alditols having, after milling and sieving, a particle size of between 250 and 1250 μm. The measuring apparatus used is a durometer ERWEKA TBH 30 GMD.

This force therefore expresses here the resistance to crushing of a tablet which is cylindrical with convex faces (13 mm radius of curvature), with a diameter of 13 mm, a thickness of 6 mm and a weight of 0.845 g, i.e., an apparent density of 1.48 g/ml.

The results show that the powder containing crystalline particles of glucopyranosyl-alditols according to the invention has a high compressibility value, which, to the knowledge of the Applicant company, has yet never been described.

Determinations of the aerated density, of the packed density and the angle of slope are achieved by an apparatus marketed by the HOSOKAWA company under the brand POWDER TESTER by applying the method recommended by the manufacturer.

Under these conditions, the powder containing crystalline particles of glucopyranosyl-alditols, with a particle size of between 250 and 1250 μm, has an aerated density of between 0.700 and 0.750 g/ml, a packed density also of between 0.700 and 0.750 g/ml, and a angle of slope of between 42 and 45°.

The following example illustrates the preparation of the powder containing crystalline particles of glucopyranosyl-alditols by using the method according to the invention.

EXAMPLE

A 70% dry matter suspension of glucopyranosyl-alditols (compound A) is prepared and is placed in an evaporation container so as to obtain a glucopyranosyl-alditol syrup with a dry matter content of about 85% (the glucopyranosyl-alditol content of compound A is shown in table 1 below, expressed as dry weight over the totality of the components of the mixture).

This glucopyranosyl-alditol syrup is placed in a storage tank at a temperature of about 135° C., from which it is continuously sampled by means of a pump which provides its dispersion as globules by means of a nozzle.

Simultaneously with the dispersion of said glucopyranosyl-alditol syrup, additional germ material is continuously introduced into the pilot scale granulator in order to achieve a weight germs/syrup ratio of about 4 parts of germs for 1 part of glucopyranosyl-alditol syrup.

The germs are obtained by continuous recycling of a fraction of the produced solidified material.

Particles of any crystalline solid of glucopyranosyl-alditols may be used to provide germs for the initial granulation.

No particular effort is made for controlling the temperature of the granulator (which remains of the order of 90° C.).

The granulator rotates at a velocity of about 6.5 revolutions per minute, its tilt is 30°, so that granules with an average diameter of about 100 μm to 50,000 μm may be obtained.

After this granulation step, said granules are matured by completing the crystallization in a maturation device (elongated rotary drum).

The thereby obtained maturated granules are submitted to rough milling and then dried in a fluidized bed by using air at 60° C. for 30 minutes.

After drying, they appear in the form of a powder containing about 6% of residual moisture (value determined according to the KARL FISHER method).

At the outlet of the roller conveyor of the fluidized bed, the dried powder is led to a conventional milling facility. The dried powder is then sieved and a portion of it is recycled as germs containing glucopyranosyl-alditols to the granulator.

The remaining powder is the powder containing the crystalline particles of glucopyranosyl-alditols according to the invention (compound B).

The following table 1 shows the glucopyranosyl-alditol compositions of compounds A and B, as well as the result of the measurements of the DSC parameters (melting point and enthalpy).

TABLE 1

|  | Compound A | Compound B |
| --- | --- | --- |
| 1,1 GPS (dry weight %) | 0.3 | 0.3 |
| 1,1 GPM (dry weight %) | 48.3 | 48.1 |
| 1,6 GPS (dry weight %) | 50.7 | 50.2 |
| DSC analysis |  |  |
| $1^{st}$ endothermal peak |  |  |
| melting temperature (° C.) | 95.39 | 99.25 |
| enthalpy (J/g) | 34.28 | 81.26 |
| $2^{nd}$ endothermal peak |  |  |
| melting temperature (° C.) | 146.24 | 125.23 |
| enthalpy (J/g) | 116.20 | 54.10 |
| Residual moisture | 2.5 | 6.0 |

The granulation of the compound A by the method according to the invention changes in no way the glucopyranosyl-alditol chemical composition.

However, it leads to the change of the melting heat profile of the compound B, which is expressed by the significant reduction of both the melting point and the enthalpy of the second endothermal peak of the compound B, and which is also accompanied by a slight reduction in the enthalpy of the first endothermal peak of said compound B.

The following Table 2 shows the results of compressibility, aerated density and packed density, angle of slope and of flow measurements for compounds A and B.

TABLE 2

|  | Compound A | Compound B |
| --- | --- | --- |
| Compressibility according to the test A (Newtons) | 26 | 317 |
| Aerated density (g/ml) | 0.936 | 0.729 |
| Packed density (g/ml) | 0.936 | 0.729 |
| Angle of slope (°) | 41 | 44 |

The method according to the invention imparts to the thereby obtained powder containing crystalline particles of glucopyranosyl-alditols a lower density than the starting product, and especially remarkable compression properties.

The invention claimed is:

1. A method for making a powder containing crystalline particles of glucopyranosyl-alditols, comprising:
preparing a mixture consisting essentially of glucopyranosyl-alditol syrup, germs containing glucopyranosyl-alditols and (glucopyranosyl-alditol)-based granules by continuous mixing of the glucopyranosyl-alditol syrup having a dry matter content of at least 80% by weight and a glucopyranosyl-alditol content of at least 95% by weight, based on dry matter, the mixing being carried out by simultaneously dispersing the glucopyranosyl-alditol syrup and the germs containing glucopyranosyl-alditols in an open rotary container containing the (glucopyranosyl-alditol)-based granules, whereby the glucopyranosyl-alditol syrup and the germs containing glucopyranosyl-alditols are mixed at a surface of the (glucopyranosyl-alditol)-based granules contained in the container;

recovering the (glucopyranosyl-alditol)-based granules from the container; and crystallizing the glucopyranosyl-alditols contained in said granules, the (glucopyranosyl-alditol)-based granules in the container being kept in motion by rotating the container.

2. The method according to claim 1, wherein the glucopyranosyl-alditol syrup is introduced into the container in a subdivided form.

3. The method according to claim 2, wherein the glucopyranosyl-alditol syrup is introduced as drops.

4. The method according to claim 2, wherein the glucopyranosyl-alditol syrup is introduced as jets.

5. The method according to claim 1, wherein an axis of rotation of the container is tilted relatively to a horizontal.

6. The method according to claim 1, wherein the (glucopyranosyl-alditol)-based granules are recovered by overflow at an outlet of the container.

7. The method according to claim 1, wherein granules with a diameter of 100 to 50,000 μm are recovered.

8. The method according to claim 1, wherein a glucopyranosyl-alditol syrup, with a dry matter content of at least 80% by weight, is brought to a temperature of at least 80° C. and is continually mixed with germs containing glucopyranosyl-alditols, wherein a germs/syrup ratio, dimensions, an orientation of an axis of rotation and a velocity of rotation of the container are selected so that a product recovered from the container appears as granules having a diameter of 100 to 50,000 μm.

9. The method according to claim 8, wherein the germs/syrup ratio is not greater than about 4/1.

10. The method according to claim 1, wherein the container is in the form of a tank or an open drum having an essentially flat bottom.

11. The method according to claim 10, wherein the axis of rotation of the container forms an angle of 25 to 45° relatively to the horizontal.

12. The method according to claim 1, wherein the recovered glucopyranosyl-alditol granules are matured so as to increase their crystallinity by maintaining the granules at a temperature of 50 to 90° C. for 20 minutes to 2 hours while keeping the granules in motion in an air stream.

13. The method according to claim 12, wherein the matured recovered granules of glucopyranosyl-alditols are milled and dried in order to obtain a residual moisture of between 2 and 10%.

14. The method according to claim 1, wherein the glucopyranosyl-alditol syrup has the glucopyranosyl-alditol content of at least 98% by weight, based on the dry matter.

15. The method according to claim 1, wherein the method is a continuous method that includes:

continuous mixing of glucopyranosyl-alditol syrup, germs containing glucopyranosyl-alditols and (glucopyranosyl-alditol)-based granules; and concurrent coating, agglomeration and induction of crystallization by allowing the agglomerated mixture to mature at a temperature below the melting point of glucopyranosyl-alditols, in order to form solid granules.

16. The method according to claim 1, wherein the (glucopyranosyl-alditol)-based granules are produced in purified form in a single step before recovering.

17. The method according to claim 1, wherein the method does not require a very high concentration of glucopyranosyl-alditols, and does not require any particular effort for monitoring or accurately measuring the temperature.

18. The method according to claim 1, wherein the method does not involve an application of a shear or kneading force.

19. A continuous method for making a powder containing crystalline particles of glucopyranosyl-alditols, consisting essentially of:

producing purified (glucopyranosyl-alditol)-based granules in a single step by preparing a mixture consisting essentially of glucopyranosyl-alditol syrup, germs containing glucopyranosyl-alditols and (glucopyranosyl-alditol)-based granules by continuous mixing of the glucopyranosyl-alditol syrup having a dry matter content of at least 80% by weight and a glucopyranosyl-alditol content of at least 95% by weight, based on dry matter, the mixing being carried out by simultaneously dispersing the glucopyranosyl-alditol syrup and the germs containing glucopyranosyl-alditols in an open rotary container containing the (glucopyranosyl-alditol)-based granules, whereby the glucopyranosyl-alditol syrup and the germs containing glucopyranosyl-alditols are mixed at a surface of the (glucopyranosyl-alditol)-based granules contained in the container;

recovering the (glucopyranosyl-alditol)-based granules from the container; and crystallizing the glucopyranosyl-alditols contained in said granules, the (glucopyranosyl-alditol)-based granules in the container being kept in motion by rotating the container.

* * * * *